United States Patent
Paul et al.

(10) Patent No.: US 10,576,027 B2
(45) Date of Patent: Mar. 3, 2020

(54) EMULSION COMPRISING A MIXTURE OF SILICONE POLYMER AND METHOD OF PREPARATION THEREOF

(71) Applicant: WACKER METROARK CHEMICALS PVT. LTD., West Bengal (IN)

(72) Inventors: Amit Kumar Paul, Kolkata (IN); Papia Chakraborty, Kolkata (IN)

(73) Assignee: WACKER METROARK CHEMICALS PVT. LTD., West Bengal (IN)

( * ) Notice: Subject to any disclaimer, the term of this patent is extended or adjusted under 35 U.S.C. 154(b) by 0 days.

(21) Appl. No.: 15/781,087

(22) PCT Filed: Dec. 20, 2016

(86) PCT No.: PCT/IB2016/057816
§ 371 (c)(1),
(2) Date: Jun. 1, 2018

(87) PCT Pub. No.: WO2017/109692
PCT Pub. Date: Jun. 29, 2017

(65) Prior Publication Data
US 2018/0353396 A1    Dec. 13, 2018

(30) Foreign Application Priority Data
Dec. 21, 2015   (IN) .................. 1315/KOL/2015

(51) Int. Cl.
| | |
|---|---|
| *A61K 8/06* | (2006.01) |
| *A61K 8/86* | (2006.01) |
| *A61K 8/892* | (2006.01) |
| *A61K 8/898* | (2006.01) |
| *A61Q 5/02* | (2006.01) |
| *A61Q 5/12* | (2006.01) |
| *A61K 8/41* | (2006.01) |

(52) U.S. Cl.
CPC ............... *A61K 8/062* (2013.01); *A61K 8/41* (2013.01); *A61K 8/86* (2013.01); *A61K 8/892* (2013.01); *A61K 8/898* (2013.01); *A61Q 5/02* (2013.01); *A61Q 5/12* (2013.01); *A61K 2800/412* (2013.01)

(58) Field of Classification Search
CPC . A61K 8/06; A61K 8/86; A61K 8/892; A61K 8/898; A61Q 5/02; A61Q 5/12
See application file for complete search history.

(56) References Cited

U.S. PATENT DOCUMENTS

| | | |
|---|---|---|
| 6,028,041 A | 2/2000 | Decoster et al. |
| 6,610,280 B2 | 8/2003 | Ainger et al. |
| 2001/0000467 A1 | 4/2001 | Murray |
| 2011/0052521 A1 | 3/2011 | Tanaka et al. |

FOREIGN PATENT DOCUMENTS

| | | |
|---|---|---|
| GB | 2540236 A | 1/2017 |
| JP | 2003-119114 A | 4/2003 |
| WO | 99/49836 A1 | 10/1999 |
| WO | 03/092639 A1 | 11/2003 |
| WO | 2012/152723 A1 | 11/2012 |
| WO | 2015/082358 A1 | 6/2015 |

OTHER PUBLICATIONS

Int'l Search Report and Written Opinion from Int'l Patent Appln. No. PCT/IB2016/057816, dated Mar. 22, 2017.
Davies, J.T., "A Quantitative Kinetic Theory of Emulsion Type. I. Physical Chemistry of the Emulsifying Agent", Gas/Liquid and Liquid/Liquid Interface (Proceedings of the International Congress of Surface Activity): 426-438 (1957).
Griffin, W., "Calculation of HLB Values of Non-Ionic Surfactants", Journal of Cosmetic Science, 5(4): 249-256 (1954).
Godfrey, K.M., "Cationic emulsifiers in cosmetics", J. Soc. Cosmetic Chemists, 17: 17-27 (1966).

*Primary Examiner* — Zohreh A Fay
(74) *Attorney, Agent, or Firm* — Merchant & Gould P.C.

(57) ABSTRACT

Present invention is related to an oil-in-water emulsion comprising a silicone mixture, a mixture of emulsifier having HLB value from 10 to 16, and the particle size of the silicone mixture in the emulsion is less than 350 nm. A method of preparing the said emulsion comprising mixing a trialkylsilyl terminated dialkylpolysiloxane of viscosity of from 40,000 to less than 100,000 mPa·s at 25° C. and an amino silicone of viscosity of from 1,000 to 15,000 mPa·s at 25° C. and amine value of from 2 to 10 mg of KOH per gram of polymer, at a temperature of 25° C. to obtain a mixed silicone fluid and emulsifying the mixed silicone fluid by using plurality of the non-ionic emulsifier to obtain an oil-in-water emulsion, wherein $D_{50}$ particle size of less than 350 nm. The invention is to use the emulsion composition in the hair cosmetic composition.

14 Claims, No Drawings

EMULSION COMPRISING A MIXTURE OF SILICONE POLYMER AND METHOD OF PREPARATION THEREOF

This application is a National Stage Application of PCT/IB2016/057816, files 20 Dec. 2016, which claims benefit of Serial No. 1315/KOL/2015, filed 21 Dec. 2015 in India and which applications are incorporated herein by reference. To the extent appropriate, a claim of priority is made to each of the above disclosed application.

FIELD OF INVENTION

The present invention relates an oil-in-water emulsion comprising a silicone mixture, a mixture of emulsifier having HLB value from 10 to 16, wherein the particle size of the silicone mixture in the emulsion is less than 350 nm. The invention also relates to a method of preparing oil-in-water emulsion comprising mixing a trialkylsilyl terminated dialkylpolysiloxane of viscosity from 40,000 to less than 100,000 mPa·s at 25° C. and an amino silicone of viscosity from 1,000 to 15,000 mPa·s at 25° C. and amine value of from 2 to 10 mg of KOH per gram of polymer, at a temperature of 25° C. to obtain a mixed silicone fluid and emulsifying the mixed silicone fluid by using plurality of the non-ionic emulsifier to obtain an oil-in-water emulsion, wherein particle size of the mixed silicone fluid in the oil-in-water emulsion is less than 350 nm.

BACKGROUND OF INVENTION AND PRIOR ART

The use of silicone as a conditioning agent is already known in the art and is commonly used. It is therefore a need for the hair treatment affecting the clean feel of the hair.

The conditioning agents most commonly used to date in shampoos are cationic polymers, silicones and/or silicone derivatives which, in effect, impart to washed, dry or wet hair an ease of disentangling, softness and a smoothness which are markedly enhanced in comparison to what can be obtained with corresponding cleansing compositions which do not contain them. In addition, the silicones and/or silicone derivatives is in the form of emulsion for the best performance results.

There are few prior art that describes the silicone in the personal care composition: In WO2012152723A1 teaches about the use of a hair treatment composition to provide selective conditioning benefits to damaged hair.

In U.S. Pat. No. 6,610,280B2 describes a hair treatment composition containing a silicone component comprising droplets of silicone blend, the silicone blend comprising (i) from 50 to 95% by weight of the silicone component of a first silicone having a viscosity of at least 100,000 mm2/sec at 25° C., and (ii) from 5 to 50% by weight of the silicone component of a second silicone which is functionalized.

U.S. Pat. No. 6,028,041A describes a detergent and conditioning hair-care compositions comprising, in a cosmetically acceptable medium, (A) a washing base and (B) a conditioning system comprising at least one cationic polymer and a mixture of at least one aminated silicone and at least one insoluble silicone of viscosity less than or equal to 100 Pa·s (100,000 cSt). The composition here is in the form of mixture of liquid and emulsified.

WO1999049836A1 describes an aqueous hair conditioning composition comprising, in addition to water: i) at least one conditioning surfactant, and ii) emulsified particles of an amino functional silicone of the general formula: Si(CH3)3-O—[Si(CH3)2-O-]x-[Si(CH3)(R—NH—CH2CH2NH2)-O-]y-Si(CH3)3 wherein x+y is a number from about 50 to about 500, and wherein R is an alkylene group having from 2 to 5 carbon atoms; in which the amino functional silicone has a mole percent amino functionality of at least 1 mole %.

In US2001000467A1, the invention provides an aqueous shampoo composition comprising, in addition to water: i) at least one surfactant chosen from anionic, nonionic, zwitterionic or amphoteric surfactants or mixtures thereof; ii) an amino functionalized silicone; and iii) emulsified particles of an insoluble, non-amino functionalized silicone, in which the average silicone particle size of the emulsified non-amino functional silicone in the shampoo composition is less than 2 microns. Where, amino functionalized silicone is not in the emulsion.

JP3761440B2 describes a hair cosmetic comprises (A) a surfactant, (B) a polyorganosiloxane with an average polymerization degree of 1,400-2,200, and (C) an amino-modified polyorganosiloxane.

WO03092639A1 describes a hair treatment composition for cleansing and conditioning the hair or scalp containing a cleansing surfactant and a silicone component comprising droplets of silicone blend with a mean diameter greater than 5 micrometers, the silicone blend comprising a first silicone having a viscosity of less than 100,000 mm$^2$sec$^{-1}$ at 25° C., and a second silicone which is functionalized. The silicone blend with a mean droplet diameter $D_{3,2}$ of greater than 5 micrometers.

In spite of the recent developments in the field of personal care based on silicone emulsions, products are not satisfactory. The silicone emulsion that is currently being used in the personal care composition is usually having higher viscosity silicone in the emulsion which gives a good smoothness and feel properties but having the disadvantage of heavy feel and build up on the hair and incurs problem during removal from the hair while rinsing. Thus there is a need for a composition having lower viscosity silicone which will have similar good feel and smoothness properties similar to the higher viscosity silicone emulsion and also reduced heavy feel and build up. Also, the emulsions that are used in the personal care application are mainly big blob emulsions and hence the silicone deposition is not very uniform and the desired performance is not achieved. Thus, there is a requirement still at the present time a strong need for new products displaying improved performance with respect to one or more of the cosmetic properties mentioned above.

OBJECT OF INVENTION

An object of this invention is to provide an emulsion prepared by lower viscosity silicone or its mixture that will have similar feel properties with respect to the higher viscosity silicone emulsion with low emulsion particle size.

Also it is a great challenge to make a stable mechanical emulsion with an alkyl terminated siloxane and or alkyl terminated functional siloxane with the desired low particle size.

Another object of the invention is to use the emulsion composition in the hair cosmetic composition.

SUMMERY OF INVENTION

An oil-in-water emulsion having $D_{50}$ particle size (average hydrodynamic particle diameter) of less than 350 nm comprising a silicone mixture comprising a trialkylsilyl terminated dialkylpolysiloxane having a viscosity of from 40,000 to less than 100,000 mPa·s at 25° C. and an amino silicone having a viscosity of from 1,000 to 15,000 mPa·s at 25° C. and amine value of from 2 to 10 mg of KOH per gram of polymer; a mixture of emulsifier comprising one or more non-ionic emulsifier, wherein the mixture of emulsifiers has HLB value from 10 to 16, and water.

A method of preparing an emulsion comprising mixing a trialkylsilyl terminated dialkylpolysiloxane having a viscosity of from 40,000 to less than 100,000 mPa·s at 25° C. and an amino silicone having a viscosity of from 1,000 to 15,000 mPa·s at 25° C. and amine value of from 2 to 10 mg of KOH per gram of polymer, at a temperature of from 15° C. to 40° C., preferably at 25° C., to obtain a mixed silicone fluid; adding a mixture of emulsifier comprising one or more non-ionic emulsifier, wherein the mixture of emulsifiers has a HLB value from 10 to 16, to the mixed silicone fluid to obtain a silicone-emulsifier-mixture; homogenizing the silicone-emulsifier-mixture; and adding step-wise water, preferably demineralized water, to obtain an oil-in-water emulsion having $D_{50}$ particle size (average hydrodynamic particle size diameter) of less than 350 nm.

DETAILED DESCRIPTION OF THE INVENTION

According to one of the embodiments of present invention, there is provided an oil-in-water emulsion having $D_{50}$ particle size of less than 350 nm comprising a silicone mixture comprising a trialkylsilyl terminated dialkylpolysiloxane having a viscosity from 40,000 to less than 100,000 mPa·s at 25° C. and an amino silicone having a viscosity of from 1,000 to 15,000 mPa·s at 25° C. and amine value of from 2 to 10 mg of KOH per gram of polymer; a mixture of emulsifier comprising one or more non-ionic emulsifier, wherein the mixture of emulsifiers has having HLB value from 10 to 16, and water.

In the oil-in water emulsion the viscosity of the trialkylsilyl terminated dialkylpolysiloxane is preferably of from 40,000 to 70,000 mPa·s at 25° C., more preferably of from 51,000 to 70,000 mPa·s at 25° C. The aminosilicone has preferably an amine value of from 2 to 8 mg of KOH per gram of polymer, more preferably an amine value of form 3.5 to 8 mg of KOH per gram of polymer. The mixture of emulsifier further comprises one or more cationic emulsifier. The mixture of non-ionic emulsifier is preferably a mixture of alkyl ether of polyalkylene glycol and alkyl esters of polyalkylene glycol. The oil-in-water emulsion further comprises preferably a biocide.

According to another embodiment, the silicone mixture is a mixture comprising a trialkylsilyl terminated dialkylpolysiloxane having a viscosity of from 40,000 to less than 100,000 mPa·s at 25° C. and an amino silicone having a viscosity of from 1,000 to 15,000 mPa·s at 25° C. and amine value of from 2 to 10 mg of KOH per gram of polymer.

The viscosity of the fluids, its mixture and the emulsion prepared by the fluid is measured at 25° C. by Anton Paar Rheometer; model MCR101, geometry single gap cylinder: CC27 spindle and shear rate 1 s$^{-1}$ for 2 minutes at 25° C. is used for viscosity between 1000 to 15,000 mPa·s at 25° C. Anton Paar Rheometer; model MCR101, 25-6 cone (Cone-plate geometry: 25 mm dia./6° cone) and the "Zero gap" setting is made and shear rate 1 s$^{-1}$ for 2 minutes at 25° C., is used for viscosity between 40,000 to less than 100,000 mPa·s at 25° C. Three measurements are made for each sample and the viscosity value is taken at 60 secs. MCR Rheometer Series products work as per USP (US Pharmacopeial Convention) 912—Rotational Rheometer methods.

The trialkylsilyl terminated dialkylpolysiloxanes are preferably those of the formula $$R'_3SiO\ (R'_2SiO)_p SiR'_3 \qquad (I),$$

wherein R' is same or different and is a monovalent hydrocarbon radical having from 1 to 18 carbon atoms and p is a number of from 500 to 2000, preferably of from 1000 to 2000.

The trialkylsilyl terminated (or end-blocked or a,ω position) dialkylpolysiloxaneshave a viscosity of from 40,000 to less than 100,000 mPa·s at 25° C., preferably a viscosity of from 40,000 mPa·s to 70,000 mPa·s at 25° C., more preferably a viscosity of from 51,000 to 70,000 mPa·s at 25° C. The trialkylsilyl terminated dialkylpolysiloxanes have less than 100 ppm by weight and more preferably less than 70 ppm by weight, of hydroxy or methoxy terminated dialkylpolysiloxanes or mixture of both hydroxyl and methoxy terminated dialkylpolysiloxanes. The trialkylsilyl terminated dialkylpolysiloxane according to the invention are preferably linear but may contain additionally to the R'2SiO$_{2/2}$ units (D-units) in formula (I) RSiO$_{3/2}$ units (T-units) or SiO$_{4/2}$ units (Q-units), wherein R' is same or different and is a monovalent hydrocarbon radical having from 1 to 18 carbon atoms.

Amino silicones are preferably those of the formula $$XR_2Si\ (OSiAR)_n(OSiR_2)_m OSiR_2X \qquad (II)$$

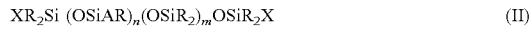

where, A is an amino radical of the formula —R$^1$—[NR$^2$—R$^3$—]$_x$NR$^2{}_2$, or the protonated amino forms of the amino radical, X is same or different and is R or a hydroxyl or an C1-C6-alkoxy group, R is same or different and is a monovalent hydrocarbon radical having from 1 to 18 carbon atoms, R$^1$ is same or different and is a C$_1$-C$_6$-alkylene radical, preferably a radical of the formula -CH$_2$CH$_2$CH$_2$— or —CH$_2$CH(CH$_3$)CH$_2$—, R$^2$ is same or different and is a hydrogen atom or a C$_1$-C$_4$-alkyl radical, preferably a hydrogen atom, R$^3$is same or different and is a C$_1$-C$_6$-alkylene radical, preferably a radical of the formula-CH$_2$CH$_2$—, where m+n is a number from 50 to about 1000, preferably in the range of about 50 to 600, x is 0 or 1. The mole percent of amine functionality is preferably in the range of from about 0.3 to about 8%.

Examples of amino silicones useful in the silicone component of the composition of the invention include trialkylsilyl terminated amino silicone.

In another embodiment, the trialkylsilyl terminated amino silicone have less than 100 ppm by weight and more preferably less than 70 ppm by weight, of hydroxy terminated aminosilicone or methoxy terminated aminosilicone or mixture of both hydroxyl and methoxy terminated amino silicone. Most preferable amino silicone is trimethylsilyl terminated aminoethylaminopropylmethylsiloxane-dimethylsiloxane copolymers. Preferably the viscosity of the amino silicones is of from 1,000 to 15,000 mPa·s at 25° C.

The amino radical A can be protonated partially or fully by adding acids to the amino silicone, wherein the salt forms of the amino radical are obtained. Examples of acids are carboxylic acids with 3 to 18 carbon atoms which can be linear or branched, such as formic acid, acetic acid, propionic acid, butyric acid, pivalic acid, sorbic acid, benzoic acid, salicylic acid. The acids are preferably used in amounts of from 0.1 to 2.0 mol per 1 mol of amino radical A in the amino silicone of formula (II).

Examples of hydrocarbons R and R' are alkyl radicals, such as the methyl, ethyl, n-propyl, isopropyl, 1-n-butyl, 2-n-butyl, isobutyl, tert-butyl, n-pentyl, isopentyl, neopentyl and tert-pentyl radical, hexyl radicals, such as the n-hexyl radical, heptyl radicals, such as the n-heptyl radical, octyl radicals, such as the n-octyl radical and isooctyl radicals, such as the 2,2,4-trimethylpentyl radical, nonyl radicals, such as the n-nonyl radicals, decyl radicals, such as the n-decyl radical, dodecyl radicals, such as the n-dodecyl radical, and octadecyl radicals, such as the n-octadecyl radical; alkenyl radicals such as the vinyl and ally radical; cycloalkyl radicals, such as the cyclopentyl, cyclohexyl, cycloheptyl and methylcyclohexyl radicals; aryl radicals, such as the phenyl, naphthyl, anthryl and phenanthryl radical; alkaryl radicals, such as the o-, m- and p-tolyl radicals, xylyl radicals and ethylphenyl radicals; and aralkyl radicals such as the benzyl radical and the α- and the β-phenylethyl radical. Most preferred is the methyl radical.

In one of the embodiments, the amine value is determined by acid-base titration using a potentiometer [Make: Veego; Model: VPT-MG]. 0.6 g of sample is taken in a 500 ml beaker and toluene-butanol 1:1 mixture is added and stirred to mix the sample thoroughly and the sample solution is titrated with a 0.1(N) HCl solution. A determination of the blank value with the toluene-butanol 1:1 mixture is also done. The calculation of the amine value is done by the above mentioned potentiometer.

The amine value is calculated according to the formula 56.11×(V−V$_{Blank}$)×N/W mg KOH/g of sample, where, V=Volume of HCl required in ml, V$_{Blank}$=Volume of HCl for blank value (without sample) with the toluene-butenol 1:1 mixture in ml; N=Normality of HCl, i.e. 0.1 N, W=Weight of the sample taken in gram.

In one of the embodiments the emulsifier is specifically selected from nonionic emulsifier or its mixtures thereof. Examples of emulsifiers which can be used in accordance with the invention are nonionic emulsifiers, ethoxylated aliphatic alcohol, polyoxyethylene surfactants, carboxylic esters, polyethylene glycol esters, anhydro sorbitol ester and its ethoxylated derivatives, glycol esters of fatty acids, carboxylic amides, monoalkanolamine condensates, polyoxyethylene fatty acid amides. The most preferable nonionic emulsifier is most preferably selected from alkyl ether of polyalkylene glycol and alkyl esters of polyalkylene glycol.

The emulsifier may be referred to as a surfactant and emulsifier and surfactant may be interchangeably used. In another embodiment, the emulsifier may further comprise the cationic emulsifiers are selected from tetra alkyl ammonium halides, tetra aryl ammonium halides, tetra alkyl aryl ammonium halides, also including salt, quaternary ammonium compound including salt, polyquaternium compound having INCI name polyquaternium 1 to 75 in use together with said non-ionic emulsifiers. The most preferable cationic emulsifier is cetyltrimethyl ammonium chloride (CTAC). Such emulsifier is obtained as Arquad from AkzoNobel, Cetyltrimethylammonium chloride solution from Sigma-Aldrich.

HLB values are typically referred to the values at room temperature (25° C.). As temperature varies, the HLB value of a surfactant/emulsifier may also vary. Calculation of HLB value of non-ionic surfactants/emulsifiers is calculated according to the equations: HLB=(E+P)/5; E=weight percentage of oxyethylene content; P=weight percentage of polyhydric alcohol content (glycerol, sorbitol, etc.) provided according to the terms of the HLB system of emulsifier classification introduced by Griffin, W. C., "Calculation of HLB Values of non-ionic Surfactants", Journal of COSMETIC SCIENCE, Vol. 5, No. 4, January 1954,249-256 (1954).

For ionic surfactants/emulsifiers, the HLB value of individual surfactant/emulsifier molecules can be calculated applying the Davies formula as described in Davies J T (1957), "A quantitative kinetic theory of emulsion type, I. Physical chemistry of the emulsifying agent", Gas/Liquid and Liquid/Liquid Interface (Proceedings of the International Congress of Surface Activity): 426-38.

According to the formula the HLB is derived by summing the hydrophilic/hydrophobic contributions afforded by the structural components of the surfactant/emulsifier.

HLB=(hydrophilic group numbers)−n(group number per CH$_2$ group)+7

A non-limiting example, Tetradecyl trimethyl ammonium chloride has the following structure:

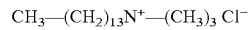

Group contribution of the hydrophobic groups: —CH$_2$/—CH$_3$ −0.475

Group contribution of the hydrophilic group: N$^+$—(CH$_3$)$_3$ Cl$^-$22.0

HLB=22−(14×0.475)+7=22.4

Approximate HLB values for some cationic emulsifier are given in Table IV, in Cationic emulsifiers in cosmetics, K. M. GODFREY, J. Soc. Cosmetic Chemists 17 17-27 (1966).

Emulsifiers mixture having HLB value in between 10-16 are suitable to make the emulsion process simpler. When two emulsifiers A and B of known HLB are thus blended for use the HLB$_{Mix}$ is said to be the required HLB for the mixture. This is expressed by the equation (W$_A$HLB$_A$+W$_B$HLB$_B$)/(W$_A$+W$_B$)=HLB$_{Mix}$, where W$_A$=the amount (weight) of the first emulsifier (A) used, and W$_B$=the amount (weight) of the second emulsifier (B); HLB$_A$, HLB$_B$=the assigned HLB values for emulsifiers A and B; HLB$_{Mix}$=the HLB of the mixture.

Most useful emulsifiers of this category are polyoxyalkylene alkyl ether, polyoxyalkylene alkyl ester,polyoxyalkylene alkylphenyl ethers and polyoxyalkylene sorbitan esters. Some useful emulsifiers having HLB value in between 10-16 are polyethylene glycol octyl ether; polyethylene glycol lauryl ether; polyethylene glycol tridecyl ether; polyethylene glycol cetyl ether; polyethylene glycol stearyl ether; polyethylene glycol nonylphenyl ether; polyethylene glycol dodecylphenyl ether; polyethylene glycol cetylphenyl ether; polyethylene glycol stearylphenyl ether; polyethylene glycol sorbitan mono stearate and polyethylene glycol sorbitan mono oleate. Non-ionic emulsifier having HLB value in-between 10-16 has a great importance in the present invention to make process simpler. In another embodiment the emulsifier is most preferably a mixture of nonionic emulsifiers.

The emulsifiers used in the invention are Steareth 6, PEG 100 Stearate, Trideceth-3, and Trideceth-10.

Steareth 6 is of the chemical formula CH$_3$(CH2)$_{18}$(OCH2CH2)$_6$—OH (HLB value 9.3), PEG 100 Stearate is of chemical formula CH$_3$(CH$_2$)$_{16}$CO(OCH$_2$CH$_2$)$_{100}$OH (HLB value 18.8), Trideceth-3 is of chemical formula CH$_3$(CH$_2$)$_{12}$(OCH$_2$CH$_2$)$_3$—OH (HLB value 6.66), and Trideceth-10 is of chemical formula CH$_3$(CH$_2$)$_{12}$(OCH$_2$CH$_2$)$_{10}$—OH (HLB value 13.25).

The composition according to the invention is an oil-in-water emulsion. In an emulsion, one liquid (the dispersed phase) is dispersed in the other (the continuous phase). According to the inventive oil-in-water emulsion the silicone mixture (the dispersed phase) is dispersed in the continuous water phase.

The stability of the emulsion is determined by the circulation of the emulsion at 45° C. for 3 months and the stability will be determined by no change in property of the emulsion. If the property changes or the oil and water phase separates at the above condition, the emulsion is said to be unstable.

The trialkylsilyl terminated dialkylpolysiloxane is in the amount of 38 to 42 percent by weight of the total oil-in-water emulsion composition, the amino silicone is in the amount of 8 to 12 percent by weight of the total oil-in water emulsion composition. The mixture of the non-ionic emulsifier is from 10 to 12 percent by weight of total oil-in-water emulsion composition. The optional cationic emulsifier is from 0.5 to 1.5 percent by weight of total oil-in-water emulsion composition. The water is from 35 to 42 percent by weight of the total oil-in-water emulsion composition. The biocide is from 0.5 to 1 percent by weight of the total oil-in-water composition.

Emulsion particle size is measured by using a device ZetaSizer from Malvern, UK, model Nano-ZS which is based on the Photon Correlation Spectroscopy (PCS) method. The $D_{50}$ value of particle size (average hydrodynamic particle diameter) is measured, wherein the evaluating algorithm is "cumulants analysis". Take 0.5 g of the emulsion sample in a 250 ml beaker, 100 ml of DM water is poured into it and then mixed properly to get the sample test solution. The sample test solution is poured in the cuvette cell and is put into the slot of the instrument to measure the particle size of the emulsion. $D_{50}$ is defined as the value of the particle diameter at 50% in the cumulative distribution. For example, if $D_{50}$=170 nm, then 50% of the particles in the sample are larger than 170 nm, and 50% smaller than 170 nm or about 50% by volume of all droplets in said emulsion is 170 nm. The $D_{50}$ particle size is expressed in volume.

According to another embodiment an oil-in-water emulsion is provided having $D_{50}$ particle size (average hydrodynamic particle diameter) of less than 350 nm comprising a silicone mixture comprising a trialkylsilyl terminated dialkylpolysiloxane having a viscosity of from 51,000 to 70,000 mPa·s at 25° C. and an amino silicone having a viscosity of from 1,000 to 15,000 mPa·s at 25° C. and amine value from 3.5 to 8 mg of KOH per gram of polymer, and a mixture of emulsifier having HLB value from 10 to 16 comprising one or more non-ionic emulsifier and water.

According to another embodiment a method of preparing the emulsion is provided comprising mixing a trialkylsilyl terminated dialkylpolysiloxane of viscosity of from 51,000 to 70,000 mPa·s at 25° C. and an amino silicone of viscosity of from 1,000 to 15,000 mPa·s at 25° C. and amine value of from 3.5 to 8 mg of KOH per gram of polymer, at a temperature of from 15° C. to 40° C., preferably at 25° C., to obtain a mixed silicone fluid, then adding a mixture of emulsifier comprising one or more non-ionic emulsifier, wherein the mixture of emulsifiers has a HLB value from 10 to 16, to the mixed silicone fluid to obtain an silicone-emulsifier-mixture, then homogenizing the silicone-emulsifier-mixture followed by adding step-wise water, preferably demineralized water, to obtain an oil-in-water emulsion having $D_{50}$ particle size (average hydrodynamic particle diameter) of less than 350 nm.

The method of preparing the emulsion further comprises adding a biocide. The method of preparation of the mixture of emulsifier is prepared by mixing one or more non-ionic emulsifier. Biocide was added for preserving the emulsion against microbial contamination. The biocide is added up to 2% of emulsion composition) for preserving emulsion against microbial contamination and obtaining the said emulsion. The quantity of the biocide depends on the type of biocide and as recommended by the manufacturer. The pH of the emulsion after neutralization is preferably 4 to 6.

The oil-in-water emulsion of the invention is preferably used in hair care compositions, preferably the amounts ranging from 3 to 10 percent by weight based on the hair care composition.

Further constituents of the hair care compositions are, for example, surfactants, fatty alcohols, rheology modifiers, pearlizers, organic acids, fragrances, preservatives, vitamins, sunscreens, salts, dyes, and further components of hair care compositions known to those skilled in the art.

The hair care compositions can be in form of shampoos, rinses, creams, or sprays. Such compositions improve both the dry and the wet combability, and also the feel to the touch in the wet and dry hair. The composition can be applied during washing, after washing, as pre- or after-treatment during bleaching or during coloring with direct or oxidation dyes, and during the permanent shaping of hair (e.g. permanent wave). The invention further provides hair-care compositions comprising emulsions that impart a better conditioning property along with other desirable properties. Better conditioning property includes but not limited to reduction of wet combing force, improvement of dry feel or smoothness, reduction of dry combing force, reduction of heavy fee, reduced build up, improvement of shine.

Measurement of Friction and Combing Force

Take the hair tresses to be tested and immerse in Pet-ether (60-80° C. boiling range) for 1 hr. After 1 hr, dry them in open air. Then wash with 100 ml of 1% of sodium lauryl ether sulfate (SLES). Dry them again in open air.

The test methods that are performed to determine the conditioning property are by measure the friction and combing force after applying silicone conditioner in shampoo on hair tresses by using Texture Analyzer (TA XT Plus) from Stable Micro Systems Machine. The metallic comb is attached horizontally and tightened with the screws. Now fix the hair tress within the clip of upper zig. The comb height is calibrated. The speed of the comb is 5 mm/s and the test is run for 10 times. The result of combing force is obtained in miliNewton. For fiction measurement, of standard hair swatch of 400 mm length is taken and is measured by using a friction probe attachment which is 60 g of weight and contact area with hair is approx. 1 sq.cm and is placed on the hair and moved at a speed of 5 mm/s to measure the friction value, the whole length of hair is measured for the friction value and the friction value thus obtained in grams is multiplied with 400 mm length to obtain the result in g.mm.

Panel Test

Effect of silicone when used as conditioner in shampoo on hair tresses manually. Take the hair tresses to be tested and immerse in Pet-ether (60-80° C. boiling range) for 1 hr. After 1 hr, dry them in open air. Then wash with 100 ml of 1% of sodium lauryl ether sulfate (SLES).Dry them again in open air. Half portion of the hair cosmetic composition (0.1 gram of composition per gram of hair) is taken to be applied and apply it along the whole length of the tress for 30 s. Keep it untouched for 30 s. Then wash it off properly. Again, apply the rest portion of the hair cosmetic composition in similar way for 60 s and keep it untouched for 60 s. Then finally wash it off with water properly.

Feel the wet softness and rate it as 4=fair, 6=good, 8=very good, 10=excellent. Count the number of stokes for detangling completely in wet condition. Allow it to dry in open air.

Feel the dry softness and rate it as 4=fair, 6=good, 8=very good, 10=excellent. Count the number of stokes for detangling completely in dry condition. Note the volume of the hair tress and rate as 4=fair, 6=good, 8=very good, 10=excellent.

Silicone Deposition Test

The amount of deposition of silicone on the hair sample after initial treatment with the hair care composition was determined using X-ray diffraction (XRD) method using SPECTRO XEPOS EDXRF spectrometer device. SPECTRO's stationary EDXRF spectrometers are based on the energy-dispersive-X-ray-fluorescence analysis method. The deposition is measured at 25° C. at 50 RH. Here the hair tresses to be tested and immerse in Pet-ether (60-80° C. boiling range) for 1 hr. After 1 hr, dry them in open air. Then wash with sodium lauryl ether sulfate (SLES). Dry them again in open air.

Half portion of the hair cosmetic composition is taken to be applied and apply it along the whole length of the tress for 30 s. Keep it untouched for 30 s. Then wash it off properly. Again, apply the rest portion of the hair cosmetic composition in similar way for 60 s and keep it untouched for 60 s. Then finally wash it off with water properly. The three hair samples for each hair care composition were blended and analyzed for % relative silicone concentration on the hair surface. XRD statistics were generated from 5 measurements discarding the highest and lowest result in ppm level by weight of hair.

Each hair sample is washed by 0.5 mL of a detergent solution having 12% sodium lauryl ether sulfate (SLES)). The detergent solution was manually distributed throughout the hair sample along the length of the hair sample from top to bottom by repeated downward motions for 30 seconds. The hair sample was then placed under running warm water, at a temperature between 37.8 to 43.3° C., and rinsed for 30 seconds. The hair sample was subsequently dried using a blow-dryer at 25° C. and at 40-50 relative humidity (RH). The washing and drying steps were repeated two times. The amounts of deposition of silicone on the hair sample after the second washes were determined using XRD.

The details of the invention, its nature and objects are explained hereunder in greater detail in relation to the following non-limiting examples.

EXAMPLE I

Inventive Examples 4 to 6 and 13-15
Non-Inventive Comparative Examples 1 to 3, 7 to 12 and 16 to 36

Transfer 450 g of amino silicone fluid (trimethylsilyl terminated aminoethylaminopropyl Methylsiloxane-dimethylsiloxane copolymers) with amine valuing of KOH/gm sample, and viscosityin mPa·s at 25° C.) (as specified in example in experimental table 1) in emulsion tank. Start stirring and under stirring condition transfer 1800 g of trimethylsilyl terminated dimethylsiloxane polymer fluid (viscosity in mPa·s at 25° C.) (as specified in example in experimental table 1) in the same tank. Mix both the fluids for 2 hrs at room temperature. In a separate tank, transfer 49 g Steareth 6, 62 g PEG 100 Stearate and heat to 60° C. Maintain the temperature until both emulsifiers become liquid. Then add 31 g Trideceth-3, 350 g Trideceth-10 (80%) (This non-ionic emulsifier mixture will have HLB value=11.25). Then add 80 g water and 6.2 g glacial acetic acid in the tank and start mixing. Continue mixing till whole mass become a creamy paste. Whole paste is transfer to emulsion tank. Homogenize for 30 minutes at room temperature. Add 79.6 g demineralized water and homogenize for 60 minutes. Add 72.7 g demineralized water and homogenize for 50 minutes. Add 197.4 g Demineralized water and homogenize for 5 minutes. Add 294.3 g demineralized water and homogenize for 5 minutes. Add 180 g demineralized water and homogenize for 5 minutes. Add 180 g demineralized water and homogenize for 5 minutes. Add 197.4 g demineralized water and homogenize for 5 minutes. Add 197.4 g demineralized water and homogenize for 3 minutes. Add 228.5 g demineralized water and homogenize for 3 minutes. Lastly add 40.5 g 2-Phenoxyethanol as a biocide and homogenize for 3 minutes.

According to the experimental table 1 in some Examples a cationic emulsifier, 45 g cetyltrimethyl ammonium chloride(CTAC), is added by mixing it into the non-ionic emulsifier mixture. The HLB value of the mixture of cationic and non-ionic emulsifiers is between 10 and 16.

The HLB value of the mixture of non-ionic emulsifiers and cationic emulsifier is also between 10 and 16.

EXPERIMENTAL TABLE 1

Inventive Examples 4-6 and 13-15 non-inventive comparative examples 1-3, 7-12, 16-36
HLB Value = 11.25 of mixture of emulsifiers as described in example I

| | Trimethylsilyl terminated dimethylsiloxane polymer | | | trimethylsilyl terminated aminoethylaminopropylMethylsiloxane - dimethylsiloxane copolymers | | | | | | | |
|---|---|---|---|---|---|---|---|---|---|---|---|
| | Viscosity in mPa · s at 25° C. | | | Viscosity in mPa · s at 25° C. | | | Amine Value (mg of KOH/g sample) | | | Particle size of emulsion | Stability of Emulsion |
| Ex. No. | <40000 | >100000 | 40000-70000 | <4000 | 4000-8000 | >10000 | 1 | 7 | 20 | Other Ingredient | (nm) | |
| 1 | | | 61500 | 1500 | | | 1.1 | | | | 500 | Stable |
| 2 | | | 61000 | | 5100 | | 0.9 | | | | 640 | Stable |
| 3 | | | 61500 | | | 12000 | 1.2 | | | | 900 | Stable |
| 4 | | | 61500 | 1600 | | | | 7.1 | | | 175 | Stable |
| 5 | | | 61500 | | 5600 | | | 7.2 | | | 170 | Stable |
| 6 | | | 61500 | | | 13500 | | 6.9 | | | 190 | Stable |
| 7 | | | 61500 | 1450 | | | | | 21.2 | | 150 | Stable |
| 8 | | | 61500 | | 5900 | | | | 20.8 | | 162 | Stable |
| 9 | | | 61500 | | | 14000 | | | 20.2 | | 170 | Stable |
| 10 | | | 61500 | 1500 | | | 1.1 | | | CTAC (45 g) | 600 | Stable |
| 11 | | | 61000 | | 5100 | | 0.9 | | | CTAC (45 g) | 720 | Stable |
| 12 | | | 61500 | | | 12000 | 1.2 | | | CTAC (45 g) | 980 | Stable |
| 13 | | | 61500 | 1600 | | | | 7.1 | | CTAC (45 g) | 181 | Stable |
| 14 | | | 61500 | | 5600 | | | 7.2 | | CTAC (45 g) | 177 | Stable |

EXPERIMENTAL TABLE 1-continued

Inventive Examples 4-6 and 13-15 non-inventive comparative examples 1-3, 7-12, 16-36
HLB Value = 11.25 of mixture of emulsifiers as described in example I

| | Trimethylsilyl terminated dimethylsiloxane polymer | | | trimethylsilyl terminated aminoethylaminopropylMethylsiloxane - dimethylsiloxane copolymers | | | | | | | | |
|---|---|---|---|---|---|---|---|---|---|---|---|---|
| | Viscosity in mPa · s at 25° C. | | | Viscosity in mPa · s at 25° C. | | | Amine Value (mg of KOH/g sample) | | | | Particle size of emulsion (nm) | Stability of Emulsion |
| Exp. No. | <40000 | >100000 | 40000-70000 | <4000 | 4000-8000 | >10000 | 1 | 7 | 20 | Other Ingredient | | |
| 15 | | 61500 | | | | 13500 | | 6.9 | | CTAC (45 g) | 196 | Stable |
| 16 | | 61500 | | 1450 | | | | | 21.2 | CTAC (45 g) | 160 | Stable |
| 17 | | 61500 | | | 5900 | | | | 20.8 | CTAC (45 g) | 170 | Stable |
| 18 | | 61500 | | | | 14000 | | | 20.2 | CTAC (45 g) | 174 | Stable |
| 19 | 38000 | | | 1500 | | | 1.1 | | | | 452 | Stable |
| 20 | 38000 | | | | 5100 | | 0.9 | | | | 615 | Stable |
| 21 | 38000 | | | | | 12000 | 1.2 | | | | 870 | Stable |
| 22 | 38000 | | | 1600 | | | | 7.1 | | | 170 | Stable |
| 23 | 38000 | | | | 5600 | | | 7.2 | | | 163 | Stable |
| 24 | 38000 | | | | | 13500 | | 6.9 | | | 180 | stable |
| 25 | 38000 | | | 1450 | | | | | 21.2 | | 152 | Stable |
| 26 | 38000 | | | | 5900 | | | | 20.8 | | 168 | stable |
| 27 | 38000 | | | | | 14000 | | | 20.2 | | 158 | Stable |
| 28 | | 150000 | | 1500 | | | 1.1 | | | | 500 | Stable |
| 29 | | 150000 | | | 5100 | | 0.9 | | | | 640 | Stable |
| 30 | | 150000 | | | | 12000 | 1.2 | | | | 900 | Stable |
| 31 | | 150000 | | 1600 | | | | 7.1 | | | 375 | Stable |
| 32 | | 150000 | | | 5600 | | | 7.2 | | | 370 | Stable |
| 33 | | 150000 | | | | 13500 | | 6.9 | | | 390 | stable |
| 34 | | 150000 | | 1450 | | | | | 21.2 | | 450 | Stable |
| 35 | | 150000 | | | 5900 | | | | 20.8 | | 462 | stable |
| 36 | | 150000 | | | | 14000 | | | 20.2 | | 470 | Stable |

EXAMPLE II

Non-inventive Comparative Examples II (HLB Value=8.44 of Mixture of Emulsifiers)

Transfer 450 g of amino silicone fluid (trimethylsilyl terminated aminoethylaminopropylMethylsiloxane-dimethylsiloxane copolymers)with amine value in mg of KOH/gm sample, and viscosity in mPa·s at 25° C.) (as specified in example in experimental table 2) in emulsion tank. Start stirring and under stirring condition transfer 1800 g of trimethylsilyl terminated dimethylsiloxane polymer fluid (viscosity in mPa·s at 25° C.) (as specified in example) in the same tank. Mix both the fluids for 2 hrs at room temperature. In a separate tank, transfer 49 g Steareth 6, 30 g PEG 100 Stearate and heat to 60° C. Maintain the temperature till both emulsifiers become liquid. Then add 300 g Trideceth-3, 100 g Trideceth-10 (80%) (This mixture will have HLB value=8.44). Then add 80 g water and 6.2 g glacial acetic acid in the tank and start mixing. Continue mixing till whole mass become a creamy paste. Whole paste is transfer to emulsion tank. Homogenize for 30 minutes at room temperature. Add 79.6 g demineralized water and homogenize for 60 minutes. Add 72.7 g demineralized water and homogenize for 50 minutes. Add 197.4 g Demineralized water and homogenize for 5 minutes. Add 294.3 g demineralized water and homogenize for 5 minutes. Add 180 g demineralized water and homogenize for 5 minutes. Add 180 g demineralized water and homogenize for 5 minutes. Add 197.4 g demineralized water and homogenize for 5 minutes. Add 197.4 g demineralized water and homogenize for 3 minutes. Add 228.5 g demineralized water and homogenize for 3 minutes. Lastly add 40.5 g 2-Phenoxyethanol as a biocide and homogenize for 3 minutes.

EXPERIMENTAL TABLE 2

(Non-inventive Comparative Examples)
HLB VALUE = 8.44 of mixture of emulsifiers as described in example II:

| | Trimethylsilyl terminated dimethylsiloxane polymer | | | trimethylsilyl terminated aminoethylaminopropylMethylsiloxane - dimethylsiloxane copolymers | | | | | | | | |
|---|---|---|---|---|---|---|---|---|---|---|---|---|
| | Viscosity in mPa · s at 25 ° C. | | | Viscosity in mPa · s at 25 ° C. | | | Amine Value (mg of KOH/g sample) | | | | Particle size of emulsion (nm) | Stability of Emulsion |
| Ex. No. | <40000 | >100000 | 40000-70000 | <4000 | 4000-8000 | >10000 | 1 | 7 | 20 | Other Ingredient | | |
| 37 | | 61500 | | 1500 | | | 1.1 | | | | 1702 | unstable |
| 38 | | 61000 | | | 5100 | | .9 | | | | 1620 | unstable |
| 39 | | 61500 | | | | 12000 | 1.2 | | | | 1935 | unstable |

EXPERIMENTAL TABLE 2-continued (Non-inventive Comparative Examples)
HLB VALUE = 8.44 of mixture of emulsifiers as described in example II:

| | Trimethylsilyl terminated dimethylsiloxane polymer | | | trimethylsilyl terminated aminoethylaminopropylMethylsiloxane - dimethylsiloxane copolymers | | | | | | | | |
|---|---|---|---|---|---|---|---|---|---|---|---|---|
| | Viscosity in mPa · s at 25° C. | | | Viscosity in mPa · s at 25° C. | | | Amine Value (mg of KOH/g sample) | | | Other Ingredient | Particle size of emulsion (nm) | Stability of Emulsion |
| Ex. No. | <40000 | >100000 | 40000-70000 | <4000 | 4000-8000 | >10000 | 1 | 7 | 20 | | | |
| 40 | | | 61500 | 1600 | | | | 7.1 | | | 1242 | unstable |
| 41 | | | 61500 | | 5600 | | | 7.2 | | | 1135 | unstable |
| 42 | | | 61500 | | | 13500 | | 6.9 | | | 1270 | unstable |
| 43 | | | 61500 | 1450 | | | | | 21.2 | | 1157 | unstable |
| 44 | | | 61500 | | 5900 | | | | 20.8 | | 1060 | unstable |
| 45 | | | 61500 | | | 14000 | | | 20.2 | | 1035 | unstable |
| 46 | | | 61500 | 1500 | | | 1.1 | | | CTAC | 1620 | unstable |
| 47 | | | 61000 | | 5100 | | .9 | | | CTAC | 1522 | unstable |
| 48 | | | 61500 | | | 12000 | 1.2 | | | CTAC | 2055 | unstable |
| 49 | | | 61500 | 1600 | | | | 7.1 | | CTAC | 555 | unstable |
| 50 | | | 61500 | | 5600 | | | 7.2 | | CTAC | 646 | unstable |
| 51 | | | 61500 | | | 13500 | | 6.9 | | CTAC | 574 | unstable |
| 52 | | | 61500 | 1450 | | | | | 21.2 | CTAC | 856 | unstable |
| 53 | | | 61500 | | 5900 | | | | 20.8 | CTAC | 778 | unstable |
| 54 | | | 61500 | | | 14000 | | | 20.2 | CTAC | 865 | unstable |
| 55 | 38000 | | | | 5500 | | | 7.3 | | | 1132 | unstable |
| 56 | | 150000 | | | 5500 | | | 7.1 | | | 1325 | unstable |

For emulsion of experiment no. 37 to 56 the performance tests are not performed as these emulsions are unstable and hence difficult for performance evaluation. Since the emulsions are not stable for HLB value 8.44, the experiments with amino silicone variation in amino number and viscosity with trialkylsilyl terminated dialkylpolysiloxane of viscosity 38000 and 150000 mPa·s at 25° C. are not further performed.

EXAMPLE III

Non-inventive Comparative Examples (HLB Value=16.474 of Mixture of Emulsifiers)

Transfer 450 g of amino silicone fluid (trimethylsilyl terminated aminoethylaminopropylMethylsiloxane-dimethylsiloxane copolymers) with amine value in mg of KOH/gm sample, and viscosity in mPa·s at 25° C.) (as specified in example in experimental table 3) in emulsion tank. Start stirring and under stirring condition transfer 1800 g of trimethylsilyl terminated dimethylsiloxane polymer fluid (viscosity in mPa·s at 25° C.) (as specified in example) in the same tank. Mix both the fluids for 2 hrs at room temperature. In a separate tank, transfer 49 g Steareth 6, 350 g PEG 100 Stearate and heat to 60° C. Maintain the temperature till both emulsifiers become liquid. Then add 31 g Trideceth-3, 50 g Trideceth-10 (80%) (This mixture will have HLB value=16.474). Then add 180 g water and 6.2 g glacial acetic acid in the tank and start mixing. Continue mixing till whole mass become a creamy paste. Whole paste is transfer to emulsion tank. Homogenize for 30 minutes at room temperature. Add 179.6 g demineralized water and homogenize for 60 minutes. Add 172.7 g demineralized water and homogenize for 50 minutes. Add 297.4 g Demineralized water and homogenize for 5 minutes. Add 394.3 g demineralized water and homogenize for 5 minutes. Add 280 g demineralized water and homogenize for 5 minutes. Add 280 g demineralized water and homogenize for 5 minutes. Add 297.4 g demineralized water and homogenize for 5 minutes. Add 297.4 g demineralized water and homogenize for 3 minutes. Add 328.5 g demineralized water and homogenize for 3 minutes. Lastly add 40.5 g 2-Phenoxyethanol as a biocide and homogenize for 3 minutes.

EXPERIMENTAL TABLE 3

(Non-inventive Comparative Examples)
HLB VALUE = 16.474 of mixture of emulsifiers as described in example III

| | Trimethylsilyl terminated dimethylsiloxane polymer | | | trimethylsilyl terminated aminoethylaminopropylMethylsiloxane - dimethylsiloxane copolymers | | | | | | | | |
|---|---|---|---|---|---|---|---|---|---|---|---|---|
| | Viscosity in mPa · s at 25° C. | | | Viscosity in mPa · s at 25° C. | | | Amine Value (mg of KOH/g sample) | | | Other Ingredient | Particle size of emulsion (nm) | Stability of Emulsion |
| Exp. No. | <40000 | >100000 | 40000-70000 | <2000 | 4000-8000 | >10000 | 1 | 7 | 20 | | | |
| 57 | | | 61500 | 1500 | | | 1.1 | | | | 1172 | unstable |
| 58 | | | 61000 | | 5100 | | .9 | | | | 1204 | Unstable |
| 59 | | | 61500 | | | 12000 | 1.2 | | | | 1510 | Unstable |

EXPERIMENTAL TABLE 3-continued (Non-inventive Comparative Examples)
HLB VALUE = 16.474 of mixture of emulsifiers as described in example III

| | Trimethylsilyl terminated dimethylsiloxane polymer | | | trimethylsilyl terminated aminoethylaminopropylMethylsiloxane - dimethylsiloxane copolymers | | | | | | | | |
|---|---|---|---|---|---|---|---|---|---|---|---|---|
| | Viscosity in mPa · s at 25 ° C. | | | Viscosity in mPa · s at 25 ° C. | | | Amine Value (mg of KOH/g sample) | | | | Particle size of emulsion | Stability of Emulsion |
| Exp. No. | <40000 | >100000 | 40000-70000 | <2000 | 4000-8000 | >10000 | 1 | 7 | 20 | Other Ingredient | (nm) | |
| 60 | | | 61500 | 1600 | | | | 7.1 | | | 765 | Unstable |
| 61 | | | 61500 | | 5600 | | | 7.2 | | | 754 | unstable |
| 62 | | | 61500 | | | 13500 | | 6.9 | | | 815 | Unstable |
| 63 | | | 61500 | 1450 | | | | | 21.2 | | 752 | Unstable |
| 64 | | | 61500 | | 5900 | | | | 20.8 | | 774 | Unstable |
| 65 | | | 61500 | | | 14000 | | | 20.2 | | 792 | unstable |
| 66 | | | 61500 | 1500 | | | 1.1 | | | CTAC | 1152 | Unstable |
| 67 | | | 61000 | | 5100 | | .9 | | | CTAC | 1215 | Unstable |
| 68 | | | 61500 | | | 12000 | 1.2 | | | CTAC | 1570 | Unstable |
| 69 | | | 61500 | 1600 | | | | 7.1 | | CTAC | 763 | unstable |
| 70 | | | 61500 | | 5600 | | | 7.2 | | CTAC | 697 | Unstable |
| 71 | | | 61500 | | | 13500 | | 6.9 | | CTAC | 812 | Unstable |
| 72 | | | 61500 | 1450 | | | | | 21.2 | CTAC | 658 | Unstable |
| 73 | | | 61500 | | 5900 | | | | 20.8 | CTAC | 756 | Unstable |
| 74 | | | 61500 | | | 14000 | | | 20.2 | CTAC | 794 | Unstable |
| 75 | 38000 | | | | 5500 | | | 7.3 | | | 574 | Unstable |
| 76 | | 150000 | | | 5500 | | | 7.1 | | | 963 | Unstable |

For emulsion of experiment no. 57 to 76 the performance tests are not performed as these emulsions are unstable and hence difficult for performance evaluation. Since the emulsions are not stable for HLB value 16.474, the experiments with amino silicone variation in amino number and viscosity with trialkylsilyl terminated dialkylpolysiloxane of viscosity 38000 and 150000 mPa·s at 25° C. are not further performed.

As in experiment table 1, the performance test for emulsions of Experiment No 1 to 27 is performed and tabulated in performance test table by using the opaque shampoo base. There are other shampoo base compositions available for the desired formulation. The opaque shampoo base formulation is as follows:

Take demineralized water (DM water)=976 g, 4% carbopol slurry (in 1% glydant) from Lubrizol=400 g and stir for 30 minutes at temperature 60 to 65° C. Then take sodium lauryl ether sulfate (SLES) (30% active) (LES 70 from Galaxy surfactant)=1588 g and Cocamidopropyl betaine (CAPB from Galaxy surfactants) (36%)=168 g and stir for 30 minutes. Then take Glycol Mono Stearate (EGMS)=76 g and stir for 1 hour. Then add 2 hydroxy-3-(trimethylammonium) propyl ether chloride Guar gum (Jaguar C 13 S from Rhodia)=8 g and glycerine=40 g and stir for 45 minutes. Then take Rhodia MIRACARE® (Perlizer)=40 g and stir for 30 min. Then add cosmetic grade mica=6 g and stir for 1 hr. Again add 50% NaOH=12 g and DM water=80 g and stir for 30 min. Cool to room temperature and then add glydant=3.6 g, Thor's Microcare PM4 (preservative)=0.8 g and Disodium EDTA from Merk=2 g and stir for 30 min. Then add 22 g of 25% NaCl. 6% by weight of emulsion added according to Example 1 to 27 in the shampoo.

TABLE 4

PERFORMANCE TESTS

| Example/ Comparative Example | Dry Combing Force (mN) | Frictional Force (g · mm) | Panel test | Silicone deposition (in ppm by weight of hair) |
|---|---|---|---|---|
| C 1 | 13000 | 11000 | 4 | 600 |
| C 2 | 12500 | 10000 | 6 | 635 |
| C 3 | 10500 | 9000 | 4 | 643 |
| E 4 | 8000 | 8400 | 6 | 672 |
| E 5 | 5600 | 6000 | 10 | 767 |
| E 6 | 7000 | 7200 | 8 | 735 |
| C 7 | 23000 | 23500 | 8 | 430 |
| C 8 | 21500 | 22000 | 6 | 435 |
| C 9 | 21000 | 21000 | 6 | 443 |
| C 10 | 10500 | 10000 | 4 | 656 |
| C 11 | 10000 | 9000 | 6 | 680 |
| C 12 | 9500 | 8200 | 6 | 687 |
| E 13 | 5500 | 5500 | 8 | 808 |
| E 14 | 5000 | 5200 | 8 | 843 |
| E 15 | 4500 | 5000 | 8 | 880 |
| C 16 | 20500 | 18000 | 4 | 515 |
| C 17 | 18500 | 15000 | 4 | 557 |
| C 18 | 19000 | 16500 | 6 | 545 |
| C 19 | 15000 | 13000 | 6 | 600 |
| C 20 | 14500 | 15000 | 4 | 635 |
| C 21 | 13500 | 14000 | 6 | 643 |
| C 22 | 12000 | 13400 | 10 | 672 |
| C 23 | 15600 | 13000 | 8 | 767 |
| C 24 | 15000 | 12200 | 6 | 735 |
| C 25 | 25000 | 25500 | 6 | 430 |
| C 26 | 23500 | 24000 | 6 | 435 |
| C 27 | 22000 | 23000 | 4 | 443 |

Example 4, 5, 6, 13, 14 and 15 are the inventive ones as it gives the desired particle size and the desired performance result, i.e. the best results regarding dry combing force, frictional force, panel test and silicone deposition, as in Table 4.

So, it is observed from the comparative experiments 1 to 3 and 10 to 12 and 19 to 21, that if the amine value of the amino silicone is below 2, then the desired particle size and the performance results like the silicone deposition, combing force and frictional force are not achieved.

Again as in comparative experiments 7 to 9 and 16 to 18, the amine value of the amino silicone is >10 which is above the claimed range. It is observed that he particle size range is still achieved but the silicone deposition is in the range of 430 to 443 ppm by weight of hair and 515 to 545 ppm by weight of hair respectively the dry combing and frictional force are in the much higher value which is not at all desirable as per the required performance levels.

Also it is observed from experiment 22 to 24 though the amino silicone is having amine value within the claimed range the trimethylsilyl terminated dimethylsiloxane polymer is of viscosity of 38,000 mPa at 25° C., which is not in the desired range, and though the particle size is achieved the performance results are not within the required level because the value regarding the dry combing force and frictional force are much too high.

This result and experiments are non-limiting and is not restricted to this certain composition. They may vary and minor variations in composition may give similar result.

The invention claimed is:

1. An oil-in-water emulsion having $D_{50}$ particle size of less than 350 nm comprising:
   a silicone mixture comprising:
   a trialkylsilyl terminated dialkylpolysiloxane having a viscosity of from 40,000 to less than 100,000 mPa·s at 250 C. and an amino silicone having a viscosity of from 1,000 to 15,000 mPa·s at 25° C. and amine value of from 2 to 10 mg of KOH per gram of polymer;
   a mixture of emulsifiers comprising one or more non-ionic emulsifier, wherein the mixture of emulsifiers has a HLB value from 10 to 16; and
   water.

2. The oil-in-water emulsion of claim 1, wherein the viscosity of the trialkylsilyl terminated dialkylpolysiloxaneis from 40,000 to 70,000 mPa·s at 250 C.

3. The oil-in-water emulsion of claim 1, wherein the viscosity of the trialkylsilyl terminated dialkylpolysiloxane is from 51,000 to 70,000 mPa·s at 250 C.

4. The oil-in-water emulsion of claim 1, wherein the trialkylsilyl terminated dialkylpolysiloxane is having less than 100 ppm by weight of hydroxyl terminated dialkylpolysiloxane or methoxy terminated dialkylpolysiloxane or mixtures thereof.

5. The oil-in-water emulsion of claim 1, wherein the amino silicone is a trialkylsilyl terminated amino silicone.

6. The oil-in-water emulsion of claim 1, wherein the amino silicone having less than 100 ppm by weight of hydroxyl terminated amino silicone or methoxy terminated amino silicone or mixtures thereof.

7. The oil-in-water emulsion of claim 1, wherein the aminosilicone is of an amine value from 2 to 8 mg of KOH per gram of polymer.

8. The oil-in-water emulsion of any of claim 1, wherein the aminosilicone is having amine value from 3.5 to 8 mg of KOH per gram of polymer.

9. The oil-in-water emulsion of any of claim 1, wherein the mixture of emulsifier further comprises optionally one or more cationic emulsifier.

10. The oil-in-water emulsion of any of claim 1, wherein the mixture of non-ionic emulsifiers is a mixture of alkyl ether of polyalkylene glycol and alkyl esters of polyalkylene glycol.

11. The oil-in-water emulsion of any of claim 1, wherein the oil-in-water emulsion further comprises a biocide.

12. A method of preparing an oil-in-water emulsion comprising:
    mixing a trialkylsilyl terminated dialkylpolysiloxane having a viscosity of from 40,000 to less than 100,000 mPa·s at 25° C. and an amino silicone having a viscosity of from 1,000 to 15,000 mPa·s at 25° C. and amine value of from 2 to 10 mg of KOH per gram of polymer, at a temperature of from 15° C. to 40° C., preferably at 25° C., to obtain a mixed silicone fluid;
    adding a mixture of emulsifiers comprising one or more non-ionic emulsifier, wherein the mixture of emulsifiers has a HLB value from 10 to 16, to the mixed silicone fluid to obtain a silicone-emulsifier-mixture;
    homogenizing the silicone-emulsifier-mixture; and
    adding step-wise water, preferably demineralized water, to obtain an oil-in-water emulsion having D50 particle size of less than 350 nm.

13. The method of preparing the emulsion of claim 12, further comprises adding a biocide.

14. The method of preparing the emulsion of claim 12, wherein the mixture of emulsifier is prepared by mixing one or more non-ionic emulsifier.

* * * * *